(12) United States Patent
Ishihara

(10) Patent No.: US 8,905,933 B2
(45) Date of Patent: Dec. 9, 2014

(54) ULTRASONIC DIAGNOSTIC APPARATUS

(75) Inventor: Keitarou Ishihara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1538 days.

(21) Appl. No.: 12/174,365

(22) Filed: Jul. 16, 2008

(65) Prior Publication Data
US 2009/0030320 A1     Jan. 29, 2009

(30) Foreign Application Priority Data
Jul. 25, 2007  (JP) .................................. 2007-193553

(51) Int. Cl.
*A61B 8/06* (2006.01)

(52) U.S. Cl.
CPC ........................................ *A61B 8/06* (2013.01)
USPC ............................................................ 600/454

(58) Field of Classification Search
None
See application file for complete search history.

(56) References Cited

U.S. PATENT DOCUMENTS

| | | | | |
|---|---|---|---|---|
| 5,220,923 A * | 6/1993 | Hagiwara et al. | | 600/455 |
| 5,295,485 A * | 3/1994 | Shinomura et al. | | 600/443 |
| 5,320,105 A * | 6/1994 | Bonnefous et al. | | 600/454 |
| 5,429,137 A * | 7/1995 | Phelps et al. | | 600/455 |
| 5,609,155 A * | 3/1997 | Guracar | | 600/453 |
| 6,261,233 B1 * | 7/2001 | Kantorovich | | 600/454 |
| 6,350,241 B1 * | 2/2002 | Lifshitz | | 600/454 |
| 7,393,324 B2 * | 7/2008 | Satoh | | 600/437 |
| 7,758,507 B2 * | 7/2010 | Yoshikawa et al. | | 600/441 |
| 2004/0267127 A1 * | 12/2004 | Abend et al. | | 600/450 |
| 2005/0124885 A1 * | 6/2005 | Abend et al. | | 600/443 |
| 2005/0148875 A1 * | 7/2005 | Sato | | 600/453 |
| 2005/0150309 A1 * | 7/2005 | Beard | | 73/861.18 |
| 2008/0306386 A1 * | 12/2008 | Baba et al. | | 600/455 |

FOREIGN PATENT DOCUMENTS

| | | |
|---|---|---|
| JP | 1-99541 A | 4/1989 |
| JP | 5-92001 A | 4/1993 |
| JP | 5-115479 A | 5/1993 |
| JP | 2002-263105 A | 9/2002 |
| JP | 2005-110939 A | 4/2005 |

OTHER PUBLICATIONS

Japanese Office Action corresponding to Japanese Patent Application No. 2007-193553, dated Dec. 20, 2011.

* cited by examiner

*Primary Examiner* — Michael Rozanski
*Assistant Examiner* — Lawrence Laryea
(74) *Attorney, Agent, or Firm* — Sughrue Mion, PLLC

(57) ABSTRACT

An ultrasonic diagnostic apparatus capable of quantitatively obtaining a blood flow velocity unaffected by angle dependence. The apparatus includes: an ultrasonic probe including ultrasonic transducers for receiving ultrasonic echoes to output reception signals; a first movement information calculating unit for calculating first movement information on movement of a mobile element in a sound ray direction within the object based on the reception signals; a signal calculating unit for calculating azimuth direction component signals representing components of ultrasonic echoes in an azimuth direction based on the reception signals; a second movement information calculating unit for calculating second movement information on movement of the mobile element in the azimuth direction within the object based on the azimuth direction component signals; and a two-dimensional velocity calculating unit for calculating two-dimensional velocity information of the mobile element moving within the object based on the first and second movement information.

5 Claims, 5 Drawing Sheets

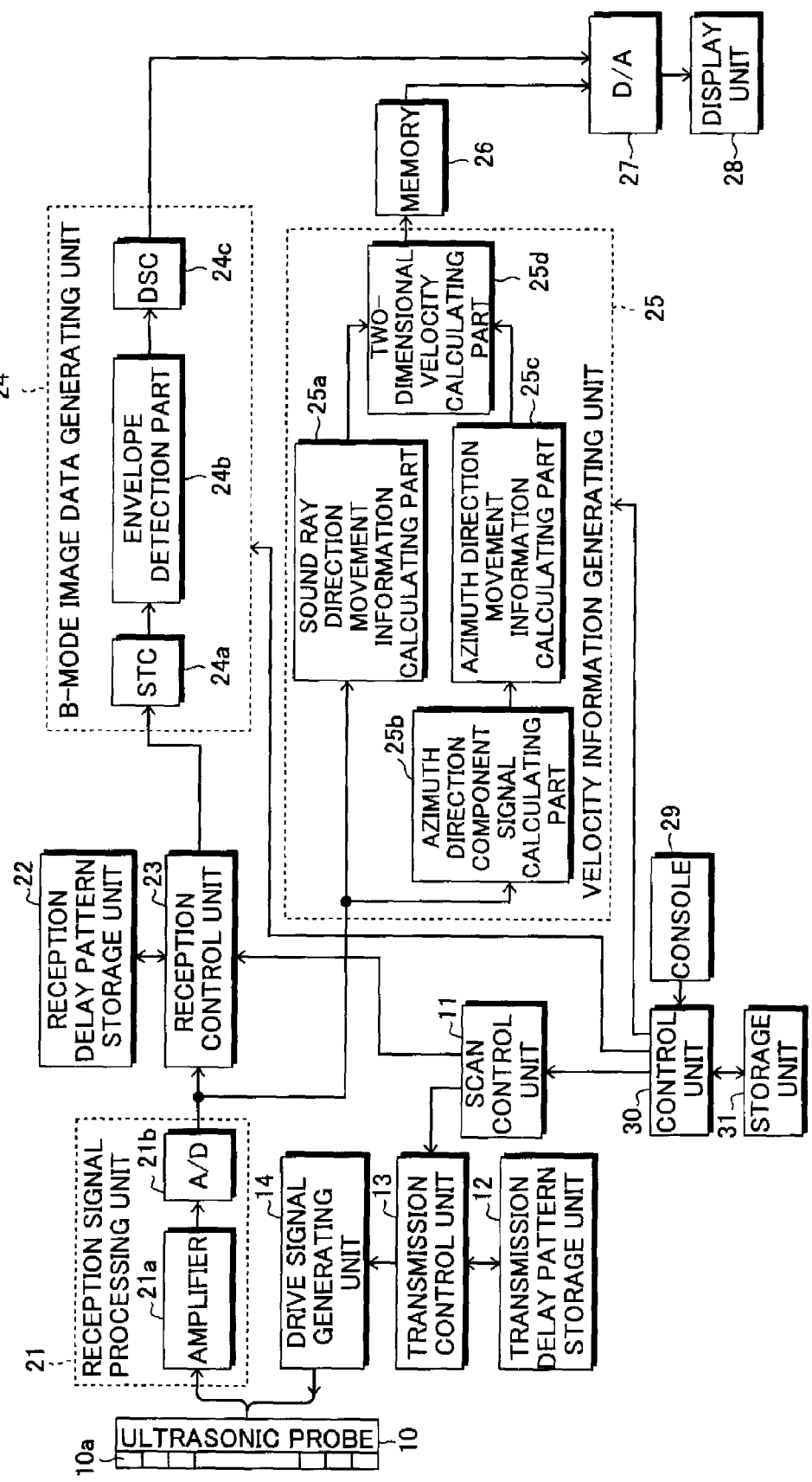

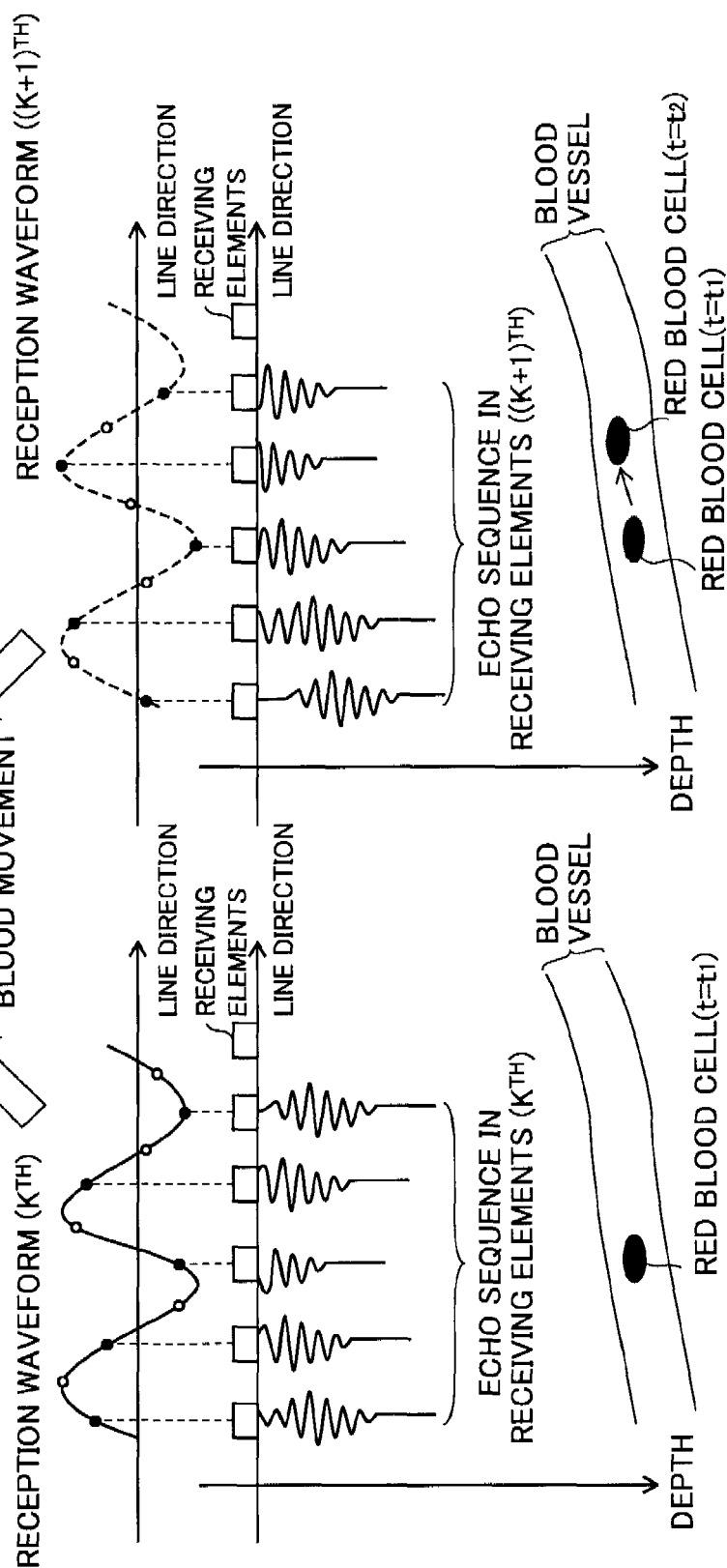

ULTRASONIC DIAGNOSTIC APPARATUS

BACKGROUND OF THE INVENTION

1. Field of the Invention

The present invention relates to an ultrasonic diagnostic apparatus for performing imaging of organs and so on within a living body by transmitting and receiving ultrasonic waves to generate ultrasonic images to be used for diagnoses.

2. Description of a Related Art

In an ultrasonic diagnostic apparatus to be used for medical application, normally, an ultrasonic probe including plural ultrasonic transducers having transmitting and receiving functions of ultrasonic waves is used. An object to be inspected is scanned by an ultrasonic beam transmitted from the plural ultrasonic transducers and the ultrasonic echoes reflected within the object are received, and thereby, image information on the object tissues is obtained based on the intensity of the ultrasonic echoes. Further, information on blood movement within the object can be obtained based on frequency shift information due to the Doppler effect contained in the ultrasonic echoes.

Currently, as a method of obtaining a real blood flow velocity, as shown in FIG. 5, real blood flow velocity "V" is calculated based on velocity component "Vy" in a sound ray direction obtained according to the Doppler effect by calculating an angle (Doppler angle) "θ" formed by the sound ray direction and the blood flow direction. For example, the real blood flow velocity "V" can be calculated using the following equation.

$$V = Vy/\cos\theta$$

However, near the location where the Doppler angle θ is 90°, an error of the calculated blood flow velocity "V" becomes greater, or it becomes impossible to obtain the blood flow velocity "V".

As a related technology, Japanese Patent Application Publication JP-A-5-115479 discloses an ultrasonic diagnostic apparatus aimed to obtain two dimensional blood flow velocity and amount of tissue displacement with high accuracy in real time, and to obtain signals having intensity according to the reflection intensity even when ultrasonic waves are diagonally reflected. The ultrasonic diagnostic apparatus includes plural weighted addition means for setting directions of reception beams to directions different from one another, and obtains components of the blood flow velocity and/or amount of tissue displacement in the directions of the respective reception beams based on the respective added signals and combines these line segments to obtain and display the blood flow velocity and/or amount of tissue displacement as two-dimensional vector quantities.

Further, Japanese Patent Application Publication JP-P2005-110939A discloses an observation apparatus aimed to obtain the state of the flow within an observation surface that is reasonable to some degree in practice under a constraint that only information on a beam direction velocity component obtained by the Doppler method using a single beam can be obtained. The observation apparatus calculates a flow rate function by integrating a beam direction velocity component at the respective points obtained by the Doppler method along the path orthogonal to the beam, obtains an integration value of only positive values and an integration value of only negative values of the beam direction velocity component along the path, considers the smaller one of the integration values as a flow rate of vortex, obtains the velocity component of the vortex in the beam direction from the ratio of the flow rate of vortex to the larger one of them, calculates a flow function of vortex by considering the vortex as a two-dimensional flow, and further, calculates the velocity component of the vortex in the direction orthogonal to the beam from the flow function.

However, in JP-A-5-115479 and JP-P2005-110939A, the correction based on the angle is performed on the respective velocity components obtained by the Doppler method, and therefore, the calculated blood flow velocity has angle dependence. That is, calculation is impossible when the Doppler angle is 90°, and the result is not the real blood flow velocity. Further, other methods of obtaining the real blood flow velocity using a two-dimensional array probe or a cross beam system are considerable, but the methods are impractical because large-scaled apparatuses are necessary therefor.

SUMMARY OF THE INVENTION

The present invention has been achieved in view of the above-mentioned problems. A purpose of the present invention is to provide an ultrasonic diagnostic apparatus capable of quantitatively obtaining a blood flow velocity unaffected by angle dependence without a scale of the apparatus being so much enlarged.

In order to accomplish the above-mentioned purpose, an ultrasonic diagnostic apparatus according to one aspect of the present invention includes: an ultrasonic probe including plural ultrasonic transducers for transmitting ultrasonic waves toward an object to be inspected and receiving ultrasonic echoes reflected within the object to output reception signals, respectively; first movement information calculating means for calculating first movement information on movement of a mobile element in a sound ray direction within the object based on the reception signals respectively outputted from the plural ultrasonic transducers; signal calculating means for calculating azimuth direction component signals representing components of ultrasonic echoes in an azimuth direction orthogonal to the sound ray direction based on the reception signals respectively outputted from the plural ultrasonic transducers; second movement information calculating means for calculating second movement information on movement of the mobile element in the azimuth direction within the object based on the azimuth direction component signals calculated by the signal calculating means; and two-dimensional velocity calculating means for calculating two-dimensional velocity information of the mobile element moving within the object based on the first and second movement information respectively calculated by the first and second movement information calculating means.

According to the present invention, since the azimuth direction component signals are calculated based on the reception signals respectively outputted from the plural ultrasonic transducers and the information on movement of the mobile element in the azimuth direction is calculated based on the azimuth direction component signals, the blood flow velocity unaffected by angle dependence can be quantitatively obtained without a scale of the apparatus being so much enlarged.

BRIEF DESCRIPTION OF THE DRAWINGS

FIG. 1 is a block diagram showing a configuration of an ultrasonic diagnostic apparatus according to one embodiment of the present invention;

FIGS. 2A-2C are diagrams for explanation of a principle of calculating azimuth direction component signals and azimuth direction movement information;

DESCRIPTION OF THE PREFERRED EMBODIMENTS

Figure 3A:
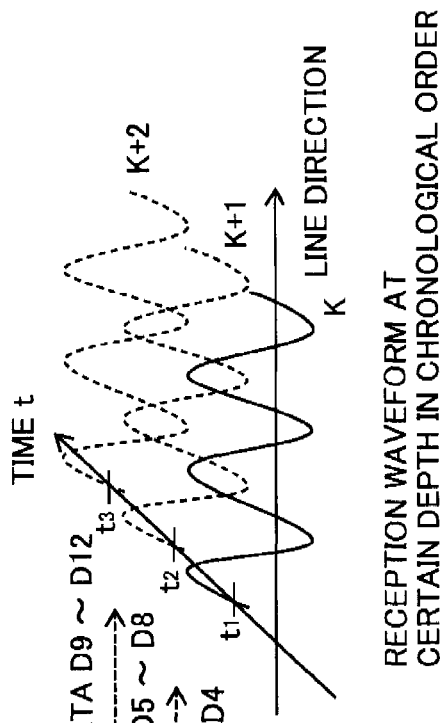
FIGS. 3A-3C are diagrams for explanation of an operation of calculating azimuth direction component signals based on reception data obtained at plural times.

Hereinafter, embodiments of the present invention will be described in detail with reference to the drawings.

FIG. 1 is a block diagram showing a configuration of an ultrasonic diagnostic apparatus according to one embodiment of the present invention. The ultrasonic diagnostic apparatus includes an ultrasonic probe 10, a scan control unit 11, a transmission delay pattern storage unit 12, a transmission control unit 13, a drive signal generating unit 14, a reception signal processing unit 21, a reception delay pattern storage unit 22, a reception control unit 23, a B-mode image data generating unit 24, a velocity information generating unit 25, a memory 26, a D/A converter 27, a display unit 28, a console 29, a control unit 30, and a storage unit 31.

The ultrasonic probe 10 to be used in contact with an object to be inspected includes plural ultrasonic transducers 10a forming a one-dimensional or two-dimensional transducer array. These ultrasonic transducers 10a transmit ultrasonic beams based on applied drive signals, and receive propagating ultrasonic echoes to output reception signals.

Each ultrasonic transducer includes a vibrator having electrodes formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like. When a pulse or continuous wave voltage is applied to the electrodes of the vibrator, the piezoelectric material expands and contracts. By the expansion and contraction, pulse or continuous wave ultrasonic waves are generated from the respective vibrators, and an ultrasonic beam is formed by composition of these ultrasonic waves. Further, the respective vibrators expand and contract by receiving the propagating ultrasonic waves to generate electric signals. These electric signals are outputted as reception signals of ultrasonic waves.

The scan control unit 11 sequentially sets the transmission directions of ultrasonic beams and the reception directions of ultrasonic echoes. The transmission delay pattern storage unit 12 has stored plural transmission delay patterns to be used when ultrasonic beams are formed. The transmission control unit 13 selects a certain pattern from among the plural delay patterns stored in the transmission delay pattern storage unit 12 according to the transmission directions set by the scan control unit 11, and sets delay times to be provided to drive signals for the plural ultrasonic transducers 10a based on the pattern.

The drive signal generating unit 14 includes plural pulsers corresponding to the plural ultrasonic transducers 10a, respectively, for example. The drive signal generating unit 14 may adjust the delay amounts of the drive signals based on the transmission delay pattern selected by the transmission control unit 13 and supply the drive signals to the ultrasonic probe 10 such that the ultrasonic waves transmitted from the plural ultrasonic transducers 10a form an ultrasonic beam, or may supply drive signals such that the ultrasonic waves transmitted at a time from the plural ultrasonic transducers 10a reach the entire imaging region of the object.

The signal processing unit 21 includes plural preamplifiers 21a and plural A/D converters 21b corresponding to the plural ultrasonic transducers 10a. The reception signals outputted from the respective ultrasonic transducers 10a are amplified in the amplifiers 21a and the analog signals outputted from the amplifiers 21a are converted into digital signals (reception data) by the A/D converters 21b. The reception data outputted from the A/D converters 21b are inputted to the reception control unit 23 and the velocity information generating unit 25.

The reception delay pattern storage unit 22 has stored plural reception delay patterns to be used when reception focus processing is performed on the reception signals outputted from the plural ultrasonic transducers 10a. The reception control unit 23 selects a certain pattern from among the plural reception delay patterns stored in the reception delay pattern storage unit 22 according to the reception directions set by the scan control unit 11, and performs reception focus processing by providing delays to the reception signals based on the pattern and adding the reception signals. By the reception focus processing, sound ray data, in which the focus of the ultrasonic echoes is narrowed, is formed.

The B-mode image data generating unit 24 generates B-mode image data as tomographic image data on tissues within the object. The B-mode image data generating unit 24 includes an STC (sensitivity time control) part 24a, an envelope detection part 24b, and a DSC (digital scan converter) 24c.

The STC part 24a performs correction of attenuation due to distance on the sound ray data formed by the reception control unit 23 according to the depths of the reflection positions of ultrasonic waves. The envelope detection part 24b performs envelope detection processing on the sound ray data corrected in the STC part 24a to generate envelope data. The DSC 24c converts (raster-converts) the sound ray data subjected to envelope detection processing by the envelope detection part 24b into image data that follows the normal scan system of television signals and performs necessary image processing such as gradation processing so as to generate B-mode image data.

The velocity information generating unit 25 generates image data representing two-dimensional velocity information of a mobile element within the object (e.g., blood within a blood vessel). The velocity information generating unit 25 includes a sound ray direction movement information calculating part 25a for calculating information on movement of a mobile element in the sound ray direction, an azimuth direction component signal calculating part 25b for calculating azimuth direction component signals representing components of ultrasonic echoes in an azimuth direction orthogonal to the sound ray direction, an azimuth direction movement information calculating part 25c for calculating information on movement of the mobile element in the azimuth direction, and a two-dimensional velocity calculating part 25d for calculating two-dimensional velocity information of the mobile element moving within the object based on the information on the movement of the mobile element in the sound ray direction and the azimuth direction.

The sound ray direction movement information calculating part 25a calculates sound ray direction movement information on movement of a mobile element in the sound ray direction within the object on the basis of the reception data outputted from the reception signal processing unit 21. For example, the sound ray direction movement information calculating part 25a performs orthogonal detection processing on the reception data, further performs correlation computation processing, processing of the PW (pulse wave) method, or the like, and thereby, calculates a Doppler shift frequency in the sound ray direction and calculates the sound ray direction movement information based thereon.

The azimuth direction component signal calculating part 25b calculates azimuth direction component signals representing the components of ultrasonic echoes in the azimuth direction orthogonal to the sound ray direction on the basis of the reception data outputted from the reception signal processing unit 21. Further, the azimuth direction movement information calculating part 25c calculates azimuth direction movement information on movement of the mobile element in the azimuth direction within the object on the basis of the azimuth direction component signals calculated by the azimuth direction component signal calculating part 25b.

FIGS. 2A-2C are diagrams for explanation of a principle of calculating the azimuth direction component signals and the azimuth direction movement information. In FIGS. 2A and 2B, the horizontal axis indicates the line direction (azimuth direction) in which plural reception devices (ultrasonic transducers) are arranged, and the vertical axis indicates the depth direction of the object. The plural reception devices (ultrasonic transducers) periodically transmit ultrasonic waves toward the object and periodically receive plural echo sequences.

FIG. 2A shows an echo sequence ($K^{th}$) received by the plural receiving devices at time $t=t_1$, and a reception waveform ($K^{th}$) according to the position of a red blood cell existing in a blood vessel of the object is obtained based thereon. Further, FIG. 2B shows an echo sequence (($K+1)^{th}$) received by the plural receiving devices at time $t=t_2$, and the position of the red blood cell has moved and a reception waveform (($K+1)^{th}$) according to the position is obtained. These reception waveforms express azimuth direction component signals representing components of ultrasonic echoes in the azimuth direction orthogonal to the sound ray direction.

In the reception waveforms shown in FIGS. 2A and 2B, black circles indicate actual measurement samples, and the number of samples is limited depending on the number of receiving devices. Accordingly, the azimuth direction component signal calculating part 25b may perform interpolation processing on the reception signals obtained by the plural receiving devices so as to add interpolation values indicated by white circles.

FIG. 2C shows superimposition of the reception waveform ($K^{th}$) at time $t=t_1$ shown in FIG. 2A and the reception waveform (($K+1)^{th}$) at time $t=t_2$ shown in FIG. 2B. As the position of the red blood cell moves, the reception waveform also moves, and the movement of reception waveform corresponds to the amount of movement of blood in the blood vessel. The reception waveform at time $t=t_1$ and the reception waveform at time $t=t_2$ have correlativity (periodicity), and these reception waveforms can be expressed by using a correlation function. Accordingly, the azimuth direction movement information calculating part 25c shown in FIG. 1 performs correlation processing on the azimuth direction component signals calculated by the azimuth direction component signal calculating part 25b so as to calculate azimuth direction movement information.

Figure 3B:
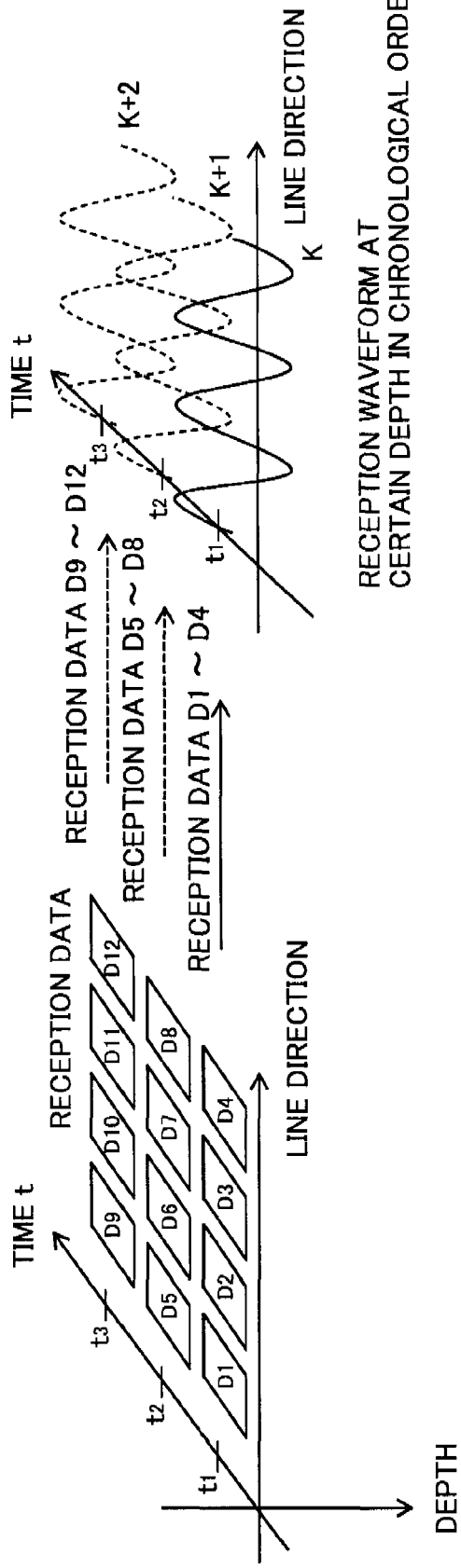
Figure 3C:
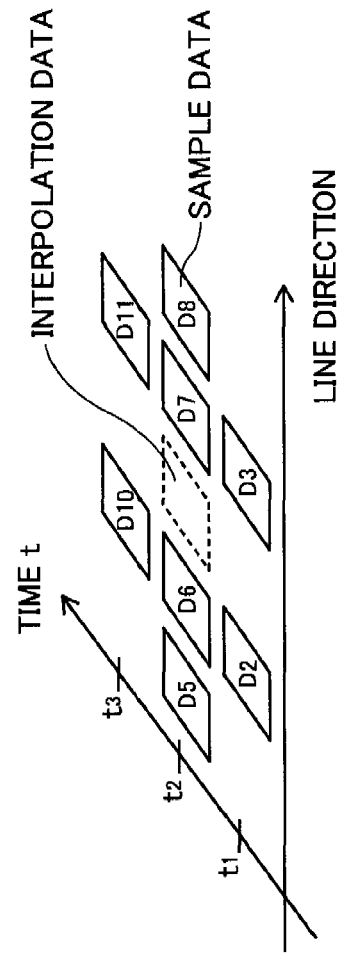

FIGS. 3A-3C are diagrams for explanation of an operation of calculating azimuth direction component signals based on reception data obtained at plural times. As shown in FIG. 3A, the azimuth direction component signal calculating part 25b (FIG. 1) generates reception data D1-D4 based on the echo sequences received at time $t=t_1$ by the plural receiving devices (here, four receiving devices) arranged in the line direction (azimuth direction), generates reception data D5-D8 based on the echo sequences received at time $t=t_2$, and generates reception data D9-D12 based on the echo sequences received at time $t=t_3$.

In practice, plural sets of reception data are generated based on ultrasonic echoes reflected at the respective depths, but FIG. 3A shows only one set of reception data D1-D12 obtained based on the ultrasonic echoes reflected at a certain depth. Further, FIG. 3B shows the $K^{th}$ reception waveform represented by the reception data D1-D4, the $(K+1)^{th}$ reception waveform represented by the reception data D5-D8, and the $(K+2)^{th}$ reception waveform represented by the reception data D9-D12 in chronological order on the basis of the ultrasonic echoes reflected at the certain depth.

Here, the azimuth direction component signal calculating part 25b may average the azimuth direction component signals calculated at plural different times to reduce noise. Further, the azimuth direction component signal calculating part 25b may perform numeric interpolation processing such as polynomial interpolation on the reception signals obtained by the plural receiving devices at plural different times, and thereby, calculate the azimuth direction component signals based on the reception signals subjected to the numeric interpolation processing.

FIG. 3C is a diagram for explanation of interpolation processing on reception data. As shown in FIG. 3C, interpolation data D13 is added to the sample data obtained based on the ultrasonic echoes that have been actually received. For example, the values of the interpolation data D13 may be calculated based on the values of the sample data D5, D6, D7, D8 and so on obtained at the same time $t=t_2$, or may be calculated based on the values of the sample data D2, D3, D6, D7, D10, D11 and so on obtained at the plural different time $t=t_1-t_3$.

Referring to FIG. 1 again, the two-dimensional velocity calculating part 25d calculates image data representing two-dimensional velocity information of the mobile element moving within the object (e.g., velocity vectors of the mobile element in a designated position) based on the sound ray direction movement information calculated by the sound ray direction movement information calculating part 25a and the azimuth direction movement information calculated by the azimuth direction movement information calculating part 25c. In this manner, the image data representing two-dimensional velocity information of the mobile element moving within the object is generated.

The memory 26 stores the two-dimensional velocity information image data outputted from the velocity information generating unit 25 according to need. The D/A converter 27 converts the B-mode image data outputted from the B-mode image data generating unit 24 and the two-dimensional velocity information image data outputted from the velocity information generating unit 25 or loaded from the memory 26 into analog image signals. The display unit 28 includes a display device such as a CRT, LCD, or the like, and displays a B-mode image of the object and a two-dimensional velocity information image of the blood in the blood vessel of the object based on the analog image signals.

The control unit 30 controls the scan control unit 11, the B-mode image data generating unit 24, and the velocity information generating unit 25 according to the operation of an operator using the console 29. The above-mentioned scan control unit 11, transmission control unit 13, reception control unit 23 to velocity information generating unit 25, and control unit 30 can be realized by a CPU and software (program). The software (program) is stored in the storage unit 31. As a recording medium in the storage unit 31, not only a built-in hard disk but also a flexible disk, MO, MT, RAM, CD-ROM, DVD-ROM, or the like may be used.

Figure 4:
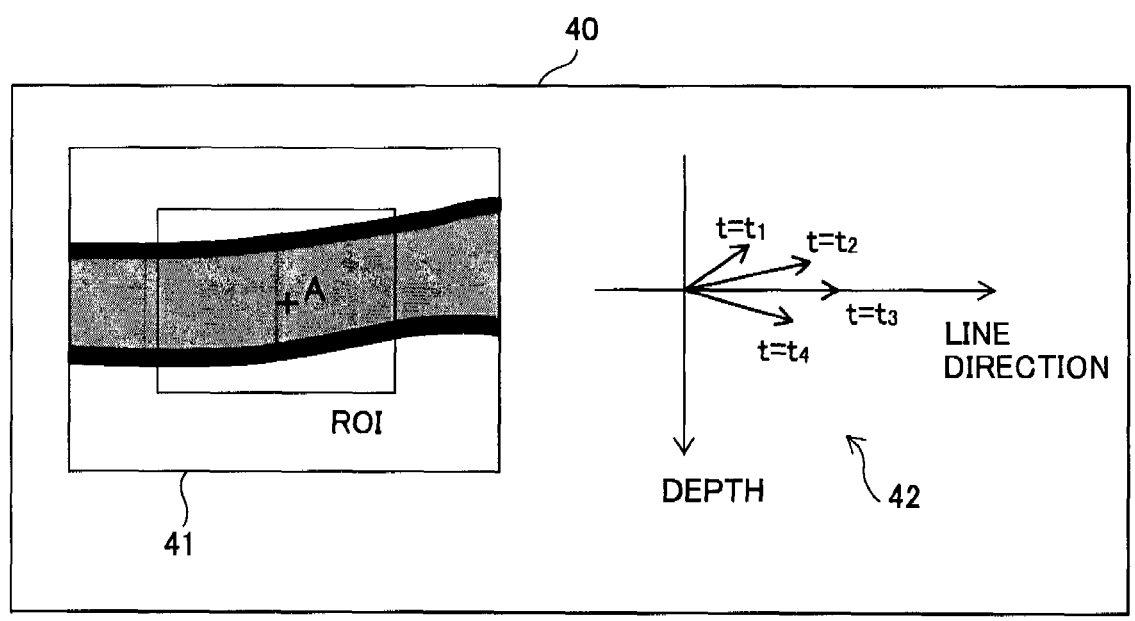
FIG. 4 shows an example of an ultrasonic image displayed on a display unit.
Figure 5:
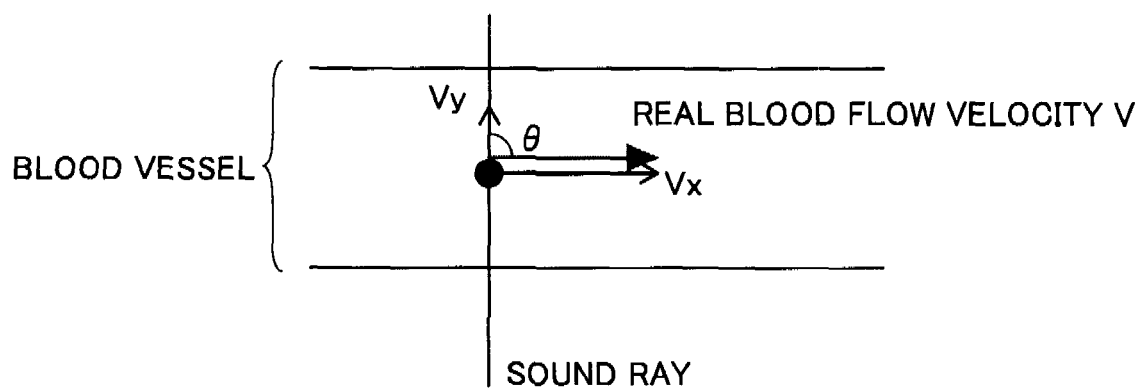
FIG. 5 shows a conventional method of obtaining a real blood flow velocity.

FIG. 4 shows an example of an ultrasonic image displayed on the display unit. This ultrasonic image 40 includes a B-mode image 41 of an object to be inspected and a two-dimensional velocity information image 42 of blood in a blood vessel of the object. When an operator uses the console 29 shown in FIG. 1 to set an ROI (region of interest) around the blood vessel displayed in the B-mode image 41 and further designates position "A" in the blood vessel, the two-dimensional velocity calculating part 25d obtains velocity vectors of the blood at the designated position "A" and causes the display unit 28 to display the two-dimensional velocity information image 42 representing the velocity vectors under the control of the control unit 30. In the two-dimensional velocity information image 42, changes of velocity vector over time at plural times $t=t_1, t_2, \ldots$ are shown.

The invention claimed is:

1. An ultrasonic diagnostic apparatus comprising:
    an ultrasonic probe including plural ultrasonic transducers for transmitting ultrasonic waves toward an object to be inspected and receiving ultrasonic echoes reflected within the object to output reception signals, respectively;
    a first movement information calculating part for calculating a Doppler shift frequency in a sound ray direction within the object based on the reception signals respectively outputted from said plural ultrasonic transducers, and calculating first movement information on movement of a mobile element in the sound ray direction based on the Doppler shift frequency;
    a signal calculating part for calculating plural azimuth direction component signals having components of ultrasonic echoes in an azimuth direction orthogonal to the sound ray direction at plural different times, each of said plural azimuth direction component signals being obtained by sampling the reception signals respectively outputted from said plural ultrasonic transducers arranged in the azimuth direction and representing a reception waveform according to a position of the mobile element in the azimuth direction;
    a second movement information calculating part for performing correlation processing on the plural azimuth direction component signals calculated by said signal calculating part to calculate second movement information on movement of the mobile element in the azimuth direction within the object; and
    a two-dimensional velocity calculating part for calculating two-dimensional velocity information of the mobile element moving within the object based on the first and second movement information respectively calculated by said first and second movement information calculating parts.

2. The ultrasonic diagnostic apparatus according to claim 1, wherein said signal calculating part averages a number of azimuth direction component signals calculated at a number of different times to obtain each of the plural azimuth direction component signals while reducing noise included therein.

3. The ultrasonic diagnostic apparatus according to claim 1, wherein said signal calculating part performs interpolation processing on the reception signals respectively outputted from said plural ultrasonic transducers, and calculates each of the plural azimuth direction component signals based on the reception signals subjected to the interpolation processing.

4. The ultrasonic diagnostic apparatus according to claim 3, wherein said signal calculating part performs numeric interpolation processing on the reception signals respectively outputted from said plural ultrasonic transducers at plural different times, and calculates the plural azimuth direction component signals based on the reception signals subjected to the numeric interpolation processing.

5. The ultrasonic diagnostic apparatus according to claim 1, further comprising:
    a B-mode image data generating unit for generating B-mode image data based on the reception signals respectively outputted from said plural ultrasonic transducers so that a display unit displays a B-mode image;
    wherein said two-dimensional velocity calculating part obtains, when a position is designated in the B-mode image displayed on said display unit, a velocity vector of the mobile element in the designated position so that said display unit displays an image representing the velocity vector.

* * * * *